United States Patent
Ito et al.

(10) Patent No.: US 7,109,933 B2
(45) Date of Patent: Sep. 19, 2006

(54) WEARABLE JACKET HAVING COMMUNICATION FUNCTION, AND ENDOSCOPE SYSTEM EMPLOYING WEARABLE JACKET

(75) Inventors: Eiichi Ito, Tokyo (JP); Mitsuhiro Matsumoto, Tokyo (JP); Koji Tsuda, Saitama-ken (JP); Masayuki Honjo, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 19 days.

(21) Appl. No.: 11/072,711

(22) Filed: Mar. 7, 2005

(65) Prior Publication Data

US 2005/0195118 A1    Sep. 8, 2005

(30) Foreign Application Priority Data

Mar. 8, 2004   (JP)   ............................. 2004-064143

(51) Int. Cl.
   *H01Q 1/12*    (2006.01)
   *A61B 5/05*    (2006.01)
(52) U.S. Cl. ...................................... 343/718; 600/410
(58) Field of Classification Search ................ 343/702, 343/718; 600/407, 410
   See application file for complete search history.

(56) References Cited

U.S. PATENT DOCUMENTS

| | | | |
|---|---|---|---|
| 3,465,103 A | 9/1969 | Lynch | 370/483 |
| 3,572,316 A | 3/1971 | Vogelman et al. | 600/484 |
| 3,682,160 A | 8/1972 | Murata | 600/302 |
| 3,683,389 A | 8/1972 | Hollis | 343/788 |
| 3,933,612 A | 1/1976 | Fischer et al. | 204/406 |
| 3,971,362 A | 7/1976 | Popo et al. | 600/302 |
| 4,027,510 A | 6/1977 | Hitebrandt | 72/37 |
| 4,090,176 A | 5/1978 | Rodeler | 340/870.28 |
| 4,177,800 A | 12/1979 | Enger | 600/302 |
| 4,198,960 A | 4/1980 | Utsugi | 600/104 |
| 4,217,045 A | 8/1980 | Ziskind | 396/17 |
| 4,262,632 A | 4/1981 | Hanton et al. | 119/51.02 |
| 4,278,077 A | 7/1981 | Mizumoto | 600/109 |
| 4,439,197 A | 3/1984 | Honda et al. | 604/891.1 |
| 4,491,865 A | 1/1985 | Danna et al. | 348/71 |

(Continued)

FOREIGN PATENT DOCUMENTS

DE    2606069    9/1976

(Continued)

OTHER PUBLICATIONS

U.S. Appl. No. 11/072,524 to Ito et al., which was filed on Mar. 7, 2005.

(Continued)

*Primary Examiner*—Shih-Chao Chen
(74) *Attorney, Agent, or Firm*—Greenblum & Bernstein, P.L.C.

(57) ABSTRACT

A wearable jacket includes a 2D-DST substrate shaped to cover a body of a subject person. The 2D-DST substrate includes a first conductive sheet, a second conductive sheet and a plurality of communication modules. The first and second conductive sheets are overlapped, and the first conductive sheet is located on the subject person side when in use. The plurality of communication modules are distributed between the first and second conductive sheets. At least one of the plurality of communication modules has a communicating system capable of communicating with an external device by receiving and/or transmitting a spatially propagating signal. One of the first and second conductive sheets on the external device side is formed with an area that allows the spatially propagating signal to pass through at a position corresponding to a location of a communication module having the communicating system.

20 Claims, 9 Drawing Sheets

U.S. PATENT DOCUMENTS

| | | | |
|---|---|---|---|
| 4,646,724 A | 3/1987 | Sato et al. | 600/109 |
| 4,679,560 A | 7/1987 | Galbraith | 607/60 |
| 4,689,621 A | 8/1987 | Kleinberg | 340/870.17 |
| 4,741,327 A | 5/1988 | Yabe | 600/130 |
| 4,844,076 A | 7/1989 | Lesho et al. | 600/302 |
| 4,917,097 A | 4/1990 | Proudian et al. | 600/463 |
| 4,936,823 A | 6/1990 | Colvin et al. | 600/7 |
| 4,951,135 A | 8/1990 | Sasagawa et al. | 348/69 |
| 5,010,412 A | 4/1991 | Garriss | 348/371 |
| 5,042,486 A | 8/1991 | Pfeiler et al. | 600/424 |
| 5,099,845 A | 3/1992 | Besz et al. | 600/424 |
| 5,166,787 A | 11/1992 | Irion | 348/75 |
| 5,167,626 A | 12/1992 | Casper et al. | 604/891.1 |
| 5,170,801 A | 12/1992 | Casper et al. | 600/582 |
| 5,187,572 A | 2/1993 | Nakamura et al. | 348/68 |
| 5,217,449 A | 6/1993 | Yuda et al. | 604/890.1 |
| 5,222,477 A | 6/1993 | Lia | 600/111 |
| 5,241,961 A | 9/1993 | Henry | 607/32 |
| 5,253,647 A | 10/1993 | Takahashi et al. | 600/424 |
| 5,267,033 A | 11/1993 | Hoshino | 348/92 |
| 5,273,025 A | 12/1993 | Sakiyama et al. | 600/145 |
| 5,279,607 A | 1/1994 | Schentag et al. | 604/890.1 |
| 5,316,015 A | 5/1994 | Sinaiko | 600/582 |
| 5,335,662 A | 8/1994 | Kimura et al. | 600/459 |
| 5,358,514 A | 10/1994 | Schulman et al. | 601/61 |
| 5,368,027 A | 11/1994 | Lubbers et al. | 600/345 |
| 5,372,133 A | 12/1994 | Hogen Esch | 600/377 |
| 5,373,840 A | 12/1994 | Knighton | 600/106 |
| 5,375,596 A | 12/1994 | Twiss et al. | 600/424 |
| 5,415,181 A | 5/1995 | Hogrefe et al. | 600/549 |
| 5,422,636 A | 6/1995 | Urbas et al. | 340/10.4 |
| 5,429,132 A | 7/1995 | Guy et al. | 600/422 |
| 5,443,066 A | 8/1995 | Dumoulin et al. | 600/424 |
| 5,448,990 A | 9/1995 | De Faria-Correa | 600/129 |
| 5,495,114 A | 2/1996 | Adair | 257/59 |
| 5,603,687 A | 2/1997 | Hori et al. | 600/166 |
| 5,604,531 A | 2/1997 | Iddan et al. | 348/76 |
| 5,662,587 A | 9/1997 | Grundfest et al. | 600/114 |
| 5,674,265 A | 10/1997 | Deschampse et al. | 607/60 |
| 5,681,020 A | 10/1997 | Buck | 248/305 |
| 5,819,736 A | 10/1998 | Avny et al. | 600/407 |
| 5,993,378 A | 11/1999 | Lemelson | 600/109 |
| 6,632,216 B1 | 10/2003 | Houzego et al. | 604/890.1 |
| 6,904,308 B1 * | 6/2005 | Frisch et al. | 600/424 |
| 7,022,066 B1 * | 4/2006 | Yokoi et al. | 600/109 |
| 2002/0173718 A1 | 11/2002 | Frisch et al. | 600/424 |
| 2003/0023150 A1 | 1/2003 | Yokoi et al. | 600/300 |
| 2004/0252729 A1 | 12/2004 | Shinoda et al. | 370/546 |
| 2005/0049462 A1 | 3/2005 | Kanazawa | 600/170 |

FOREIGN PATENT DOCUMENTS

| | | |
|---|---|---|
| DE | 2929429 | 2/1980 |
| DE | 3440177 | 11/1984 |
| DE | 4037586 | 5/1992 |
| EP | 0248867 | 2/1991 |
| EP | 5300254 | 6/1995 |
| JP | 57-45833 | 3/1982 |
| JP | 61-122845 | 6/1986 |
| JP | 62-240038 | 10/1987 |
| JP | 2-36849 | 2/1990 |
| JP | 2-159254 | 2/1990 |
| JP | 3-136636 | 11/1991 |
| JP | 3-289779 | 12/1991 |
| JP | 4-109927 | 4/1992 |
| JP | 4-144533 | 5/1992 |
| JP | 4-180736 | 6/1992 |
| JP | 5-7573 | 1/1993 |
| JP | 5-15515 | 1/1993 |
| JP | 6-114037 | 4/1994 |
| JP | 6-142081 | 5/1994 |
| JP | 6-285044 | 10/1994 |
| JP | 7-111985 | 5/1995 |
| JP | 11-341338 | 12/1999 |
| JP | 2001-46357 | 2/2001 |
| JP | 2003-19111 | 1/2003 |
| JP | 2003-38425 | 2/2003 |
| JP | 2003-188882 | 7/2003 |
| JP | 2004-7449 | 1/2004 |
| SU | 1827167 | 7/1993 |
| WO | 87/03465 | 6/1987 |
| WO | 89/01722 | 2/1989 |
| WO | 92/19148 | 11/1992 |
| WO | 92/21307 | 12/1992 |
| WO | 94/5200 | 3/1994 |

OTHER PUBLICATIONS

U.S. Appl. No. 11/072,461 to Matsumoto et al., which was filed on Mar. 7, 2005.

U.S. Appl. No. 11/072,711 to Ito et al., which was filed on Mar. 7, 2005.

"Diagnostic Imaging in 3 Easy Steps," published by Given Imaging, date unknown.

"The Heidelburg pH Capsule System Telemetric Fasting Gastric Analysis," date unknown.

Fritscher-Ravens et al., "The Wireless Capsule: New Light in the Darkness," Digestive Diseases, vol. 20, No. 2, (2002).

Bio-Medical Telemetry: Sensing and transmitting Biological Information from Animals and Man, by R. Stuart Mackay, published by John Wiley and Sons, New York, 1970, pp. 244-245.

Evan et al., "Studies of the Human Gastro-Intestinal Tract in the Ambulatory Subject using the pressure sensitive radiotelemetry capsule."

English language Abstract f DE 3440177.

Lange et al. "Heidelberger Kapsel—ein Kleinstesender fur die pH-Messung im Magen," Telefunk-Zeitung, vol. 36, No. 5, 1963, pp. 265-270.

English Language Abstract of JP 2-159254.

English Language Abstract of JP 2-36849.

English Language Abstract of JP 3-136636.

English Language Abstract of JP 5-7573.

English Language Abstract of JP 11-341338.

Manual of Photogrammetry, vol. 1, Third Edition, American Society of Photogrammetry, 1966, pp. 812-813.

P. Swain, "Wireless Capsule Endoscopy," Gut, vol. 52 (Suppl. IV), 2003, iv48-iv50, downloaded from gut.bmjjournals.com on Jul. 12, 2005.

Rowlands et al., "The Radio Pill: Telemetering from the Digestive Tract," British Communications and Electronics, Aug. 1960, pp. 598-601.

Leung et al., "Wireless Capsule Endoscopy in Chinese Patience with Suspected Small Bowel Diseases," Hong Kong Med J. vol. 10, No. 3, Jun. 2004, pp. 179-183.

Yarbrough III et al., "Evaluation of the Heidelberg pH Capsule: Method of Tubeless Gastric Analysis," The American Journal of Surgery, vol. 117, Feb. 1969, pp. 185-192.

\* cited by examiner

WEARABLE JACKET HAVING COMMUNICATION FUNCTION, AND ENDOSCOPE SYSTEM EMPLOYING WEARABLE JACKET

BACKGROUND OF THE INVENTION

The present invention relates to a wearable antenna jacket for use with an endoscope system having a communication function used for obtaining information related to a body of a subject, and an endoscope system employing such a wearable jacket.

Conventionally, when a human body of a subject is observed, an electronic endoscope is typically used. The electronic endoscope is provided with cables and optical fibers inside a flexible tube section of a scope, and at a tip thereof, an imaging element such as a CCD (Charge Coupled Device), is fixed. Such an endoscope is configured such that a relatively long flexible tube is inserted in the human cavity. Therefore, observation using such an endoscope is burdensome to the subject (examinee). Further, it is difficult to insert such an endoscope in a thin, long and meandering portion, such as intestine.

Recently, in order to decrease the burden to the subject, a system employing a capsule type endoscope has been suggested. With use of such a capsule type endoscope, it becomes easy to observe the intestine or the like.

An example of an endoscope system employing the capsule endoscope is described in Japanese Patent Provisional Publication P2003-19111 A. According to the endoscope system disclosed in the above publication, a belt having a plurality of antennas is wound around the subject (examinee). The capsule type endoscope outputs a radio wave and the belt is configured to receive the radio wave, which is used to detect a location of the capsule type endoscope. In this publication, the capsule type endoscope is described to measure condition inside the human cavity or to capture images of inner walls of the human cavity.

Each antenna mounted on the belt described in the above publication is connected to a signal recorder that controls the entire operation of the belt via lead wires and/or thin copper patterns. Such a structure has, however, several deficiencies.

For example, if each antenna is connected to the signal recorder with lead wires or cables, the antennas and the lead wires (cables) should be mounted on the belt. Therefore, for mounting each antenna, a relatively large area is required and it is difficult to mount many antennas on the belt. Because of the small number of antennas, the antennas may not cover the entire area inside the human cavity as a signal receiving area. Further, since the belt is to be wound around the body of the subject (examinee), a flexibility is required. However, if the cables (or lead wires) are mounted, the flexibility is lost. Further, if a large number of cables (lead wires) are mounted, the weight of the belt significantly increases, which increases burden to the subject (examinee). Furthermore, if the belt is frequently bent and stretched, the cables (lead wires) may be broken (disconnected).

If the antennas are connected to the signal recorder with the copper pattern, the belt is considered to be formed from a flexible PCB (printed circuit board). In this case, in comparison with the above-described structure using cables, the flexibility may be retained. However, when the PCB is used, a pattern corresponding to the elements to be mounted should be formed on a substrate, the areas for mounting the antennas may be restricted. Therefore, the antennas may not be mounted at optimum positions and/or the number of antennas may be limited. Further, if the belt is frequently bent and stretched, the pattern may be broken and disconnected.

Further to the above, the antennas are mounted on the belt and exposed to outside. Therefore, the antennas may receive signals from devices other than the capsule endoscope, which lowers an S/N (signal to noise) ratio of the image signal.

SUMMARY OF THE INVENTION

The present invention is advantageous in that an improved endoscope system employing a capsule endoscope and overcoming the above problems is provided. That is, according to the improved endoscope system, a wearable jacket is provided. The wearable jacket mounts thereon a plurality of communicating devices at desired positions, respectively, and has durability. The endoscope system may obtain image signal at a relatively high S/N ratio regardless of environmental conditions.

According to an aspect of the invention, there is provided a wearable jacket having a data communication function. The wearable jacket includes a 2D-DST substrate shaped to cover a body of a subject person. The 2D-DST substrate includes a first conductive sheet, a second conductive sheet and a plurality of communication modules. The first conductive sheet and the second conductive sheet are overlapped, and the first conductive sheet is located on the subject person's side when the wearable jacket is in use. The plurality of communication modules are distributed between the first conductive sheet and the second conductive sheet, the plurality of communication modules being capable of communicating with adjacently arranged ones of the plurality of communication modules and relaying signals making use of the pair of conductive sheets. At least one of the plurality of communication modules has a communicating system capable of communicating with an external device by receiving and/or transmitting a spatially propagating signal, one of the first and second conductive sheets on the external device side being formed with an area that allows the spatially propagating signal to pass through at a position corresponding to the communication module having the communicating system is located.

Optionally, the external device may be located on the first conductive sheet side, and the area that allows the spatially propagating signal to pass through an opening formed on the first conductive sheet, the through opening exposing at least a part of the communication system to the outside.

The communication system may be arranged on the subject person side of the first conductive sheet.

Further, the communication system includes an antenna portion, and the at least one communication module may include a circuit portion that generates a signal transmitted through the antenna portion. Further, the communication system may be stacked on the at least one communication modules, a shape of the communication system projected on a plane of the first conductive sheet being larger than at shape of the at least one communication module projected on the plane of the first conductive sheet.

Further optionally, at least one of the plurality of communication modules is provided with a sensor that detects a body function of the subject person.

Still optionally, the first conductive sheet may be formed with a through opening which allows the sensor to contact a body surface of the subject person.

Further, the 2D-DST substrate may include an insulating sheet that covers an outer surface of the first conductive sheet, the sensor contacts the body surface of the subject person with the insulating sheet therebetween.

In a particular case, the sensor may include at least one of a body temperature sensor, a sensor for measuring a breathing rate, cardiac rate or blood pressure, a blood flow sensor, a sensor for measuring oxygen saturation degree, a sensor for detecting sweat, a sensor for detecting uric acid level, a sensor for detecting occurrence of bleeding, and electrodes for cardiographic measurement.

Optionally, the wearable jacket may be provided with a data conversion system that converts values measured by the sensor into a displayable form which can be displayed on a displaying device.

Further optionally, the wearable jacket may further include a controller that controls the communication module having the communication system to transmit a received signal to the controller through the 2D-DST substrate and the communication module having the sensor to transmit measured data to the controller through the 2D-DST substrate at every predetermined period.

The wearable jacket may further include a controller that controls the communication module having the communication system to transmit a received signal to the controller through the 2D-DST substrate at every first predetermined period and the communication module having the sensor to transmit measured data to the controller through the 2D-DST substrate at every second predetermined period which is different from the first predetermined period.

Still optionally, the first predetermined period is shorter than the second predetermined period.

The wearable jacket may further include a communication module selecting system that selects an optimum communication module having the communication system from among the plurality of communication modules, wherein the selection of the optimum communication module is performed at every third predetermined period which is longer than the second predetermined period.

Optionally, the communication system may receive the spatial propagating signal carrying an image signal, the image signal being converted into a video signal which is to be transmitted to the displaying device, values measured by the sensor being incorporated in the video signal so that the converted values are displayed together with an image represented by the image signal in an overlapped manner.

According to another aspect of the invention, there is provided an endoscope system comprising a capsule endoscope having a communication function, a wearable jacket having a communication function and a displaying device. The capsule endoscope is provided with an imaging device that is inserted in a body cavity and captures an image inside the body cavity, and a wireless communicating system that transmits image data representing the captured image toward the wearable jacket. The wearable jacket may include a 2D-DST substrate shaped to cover a body of a subject person. The 2D-DST substrate may include a first conductive sheet, a second conductive sheet and a plurality of communication modules. Further, the first conductive sheet and the second conductive sheet are overlapped. The first conductive sheet is located on the subject person side when the wearable jacket is in use. The plurality of communication modules is distributed between the first conductive sheet and the second conductive sheet. The plurality of communication modules are capable of communicating with adjacently arranged ones of the plurality of communication modules and relaying signals making use of the pair of conductive sheets. At least one of the plurality of communication modules has a communicating system capable of communicating with the capsule endoscope by receiving and/or transmitting a spatially propagating signal, one of the first and second conductive sheets on the capsule endoscope side being formed with an area that allows the spatially propagating signal to pass through at a position corresponding to the location of the communication module having the communicating system.

Optionally, the wearable jacket may include a controller that selects an optimum communication module of which a signal reception amplitude is largest among the plurality of communication modules, the controller controls the selected optimum communication module to execute a communication with the capsule endoscope.

Further, the optimum communication module transmits a spatial propagating signal for supplying power to the capsule endoscope.

According to a further aspect of the invention, there is provided a wearable jacket having a data communication function, which is further provided with a 2D-DST substrate shaped to cover a body of a subject person. The 2D-DST substrate includes at least one conductive sheet, and a plurality of communication modules. The plurality of communication modules are distributed along a plane of the at least one conductive sheet, the plurality of communication modules being capable of communicating with adjacently arranged ones of the plurality of communication modules and relaying signals in accordance with the 2D-DST technology, at least one of the plurality of communication modules having a communicating system capable of communicating with an external device by receiving and/or transmitting a spatially propagating signal, the at least one conductive sheets facing the external device side and being formed with an area that allows the spatially propagating signal to pass through at a position corresponding to the communication module having the communicating system.

According to a further aspect of the invention, there is provided a wearable jacket having a data communication function, which is provided with a 2D-DST substrate shaped to cover a body of a subject person. The 2D-DST substrate includes a first conductive sheet, a second conductive sheet, and a plurality of communication modules. With this structure, the first conductive sheet and the second conductive sheet are overlapped, the plurality of communication modules being distributed between the first conductive sheet and the second conductive sheet. The plurality of communication modules are capable of communicating with adjacently arranged ones of the plurality of communication modules and relaying signals making use of at least one of the first and second conductive sheets. At least one communication module of the plurality of communication modules having a sensor capable of detecting a body function of the subject.

BRIEF DESCRIPTION OF THE ACCOMPANYING DRAWINGS

FIG. 1 schematically shows a configuration of an endoscope system according to an embodiment of the invention;

FIG. 2 schematically shows a configuration of a capsule endoscope employed in the endoscope system according to the embodiment of the invention;

DETAIL DESCRIPTION OF THE EMBODIMENTS

Referring now to the accompanying drawings, embodiments and modifications of the endoscope system will be described.

General Overview

The endoscope system according to the invention includes a jacket having an antenna function (hereinafter, referred to as an antenna jacket). The antenna jacket is provided with circuitry to obtain various data of a subject, or examinee by radio without using lead wires, cables or copper patterns. The obtainable data may include body functions (e.g., pulse, blood pressure, temperature etc.) of the subject and images of body cavities. The antenna jacket is configured to be flexible and duarable, light weight, and further realizes freedom of design, higher density of antenna arrangement, and acquisition of image signals with a high S/N ratio.

First Embodiment

Figure 1:
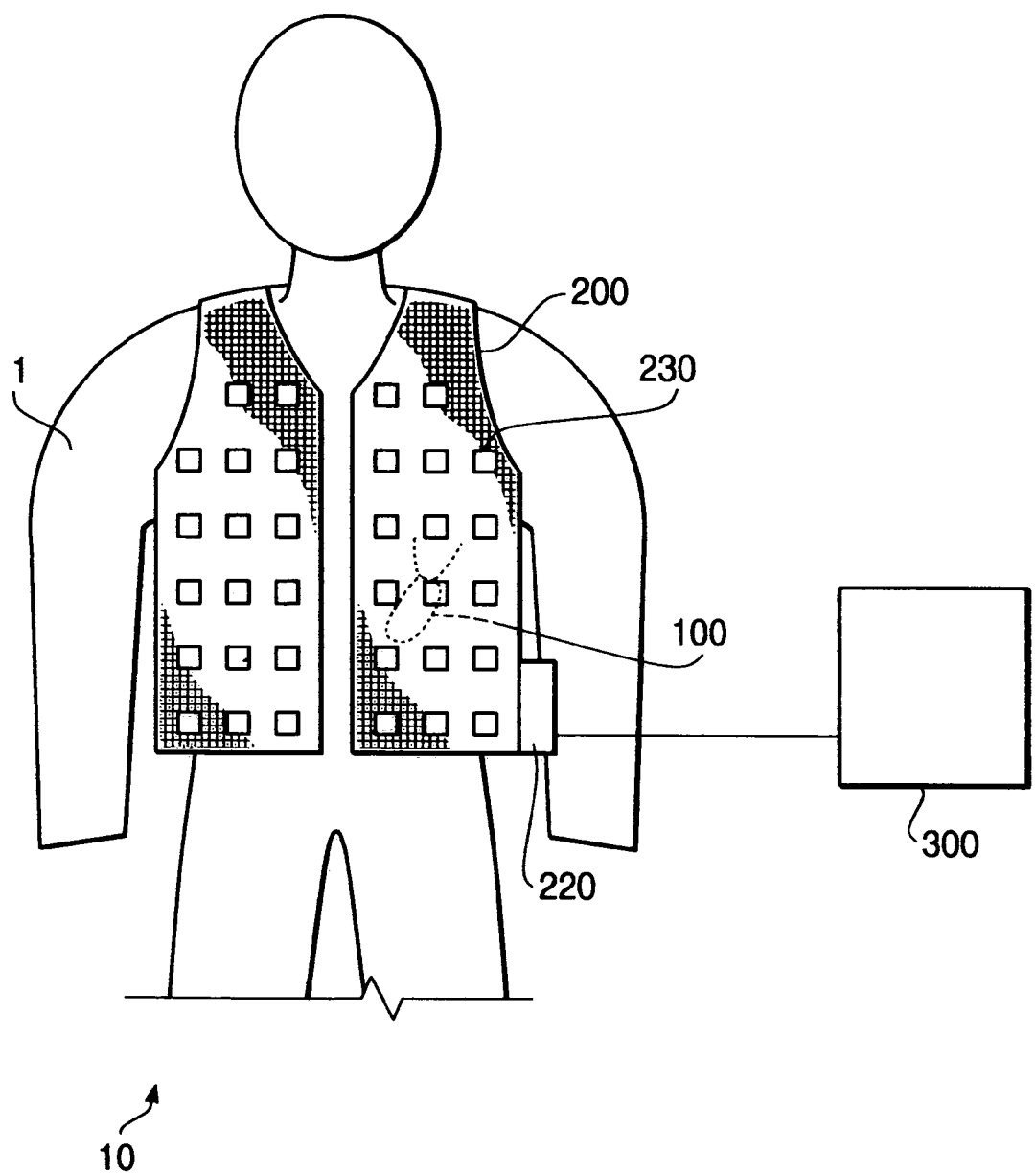

FIG. 1 schematically shows a configuration of the endoscope system 10 according to an embodiment of the invention. The endoscope system 10 is used, for example, to obtain the body functions (e.g., pulse, blood pressure, temperature etc.) and/or image information of body cavities and the like of the subject 1. Such data is used for diagnosing the subject 1.

As shown in FIG. 1, the endoscope system 10 includes a capsule endoscope 100 which is inserted (swallowed) inside the subject 1, an antenna jacket 200, and a personal computer (PC) 300. The capsule endoscope 100 captures images inside the subject 1 and outputs image data by radio. The antenna jacket 200 is provided with a plurality of antennas and circuits, and receives the image data output by the capsule endoscope 100. The antenna jacket 200 transmits the obtained signal and data related to the body functions to the PC 300. The PC 300 is provided with a display, which displays the data (e.g., image data) received from the antenna jacket 200.

Figure 2:
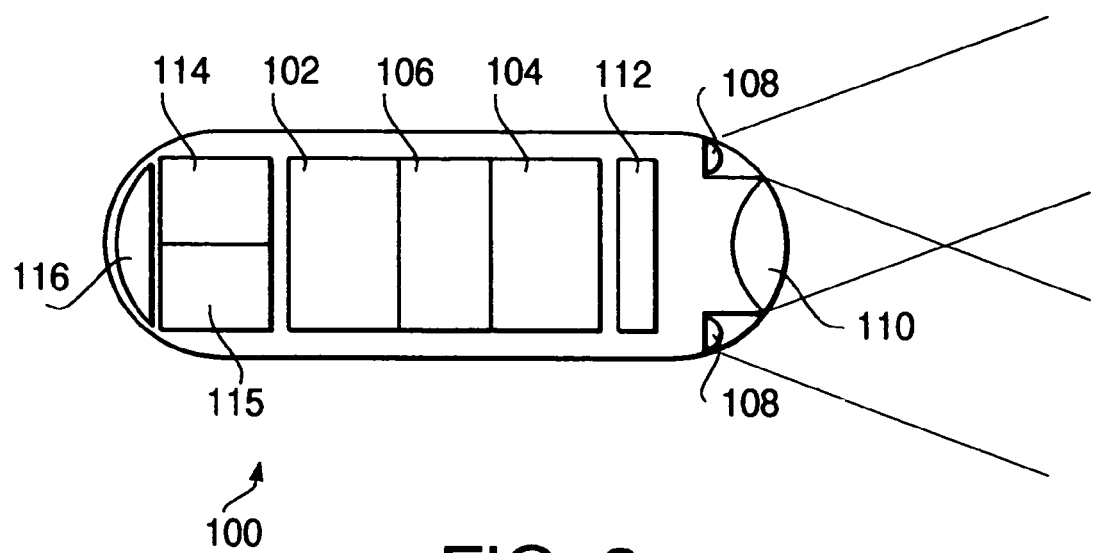

FIG. 2 is a block diagram of the capsule endoscope 100 employed in the endoscope system 10 according to the embodiment. The capsule endoscope 100 has a shape of a very small capsule, which can enter thin, long and meandering portions (e.g., a bowel) easily and capture images thereof. The capsule endoscope 100 is provided with a power unit 102 supplying power to each component of the capsule endoscope 100, a control unit 104 that controls the entire operation of the capsule endoscope 100, a memory 106 that stores various pieces of data, a pair of illuminating units 108 used for illuminating walls of the body cavity, an objective optical system 110 that converges received light to form an image on a solid-state imaging device 112 that captures images of the body cavity, a transmitting unit 114 for transmitting a radio wave carrying image data, a receiving unit 115 for receiving a radio wave transmitted from external devices, and antenna unit 116 from which the radio wave propagates.

When powered on and put into the body cavity of the subject 1, the capsule endoscope 100 illuminates inside the body cavity with the pair of illuminating units 108. The light reflected by walls of the body cavity is incident on the objective optical system 110. The objective optical system 110 and the solid sate imaging device 112 are arranged such that the objective optical system 110 forms an image on the light receiving surface of the solid state imaging device 112. The solid state image receiving device 112 applies a photoelectric conversion to the received optical image to generate an image signal corresponding to the optical image. The control unit 104 controls the transmitting unit 114 to superimpose the thus generated image signal onto a predetermined frequency signal by modulation, and transmit the modulated signal to outside through the antenna unit 116. According to the embodiment, the signal output from the antenna unit 116 is received by the antenna jacket 200.

It should be noted that the receiving unit 115 receives the radio wave from an external device, and based on signals represented by the received radio wave, the control unit 104 controls the illuminating units 108 (e.g., ON/OFF control) and other operations of the capsule endoscope 100.

Next, the structure and operation of the antenna jacket 200 will be described in detail.

The antenna jacket 200 is a wearable jacket which is formed to cover a part of the upper body of the subject 1. It should be noted that the antenna jacket 200 may be formed in various shapes and designs. For example, in FIG. 1, a vest type jacket 200 is shown, which is only an exemplar in design, and a so-called jacket having sleeves can also be used. Since the antenna jacket 200 is used for receiving the radio wave transmitted from the capsule endoscope 100 and further used for measuring body functions, it is important that the jacket 200 fits the outer shape of the subject 1.

The antenna jacket 200 is provided with a plurality of communication modules 230 distributed therein, which constitute a circuitry for obtaining the image signal transmitted by the capsule endoscope 100, a circuitry for transmitting electromagnetic waves for supplying electrical power and for transmitting control signals, and a circuitry for obtaining body functions of the subject 1. The antenna jacket 200 also has a control unit 220 which is located at a waist portion of the subject 1 when worn, and controls the entire operation of the circuitries provided to the antenna jacket 200.

Figure 3:
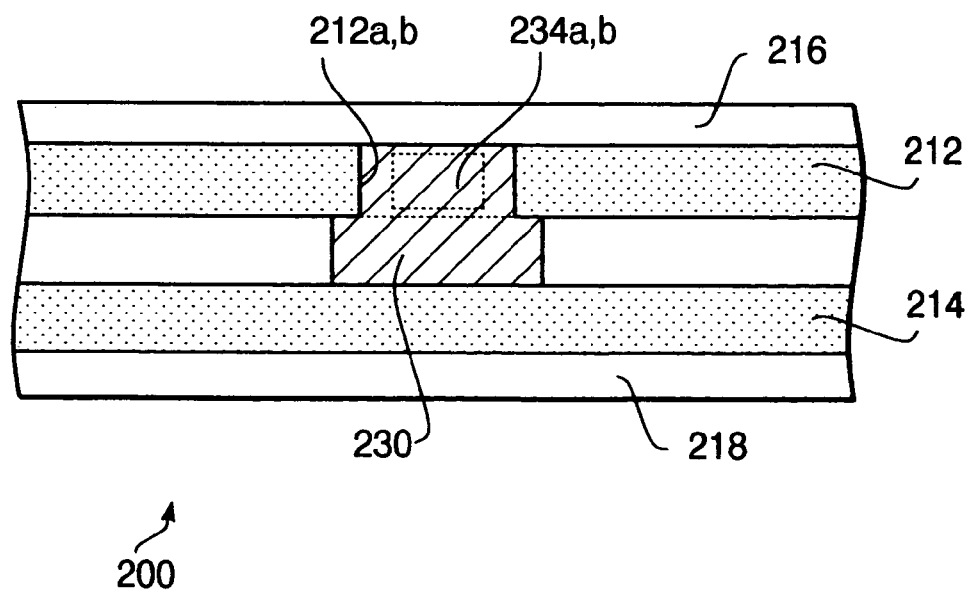
FIG. 3 shows a cross sectional structure of a part of a jacket employed in the endoscope system according to the embodiment of the invention.

FIG. 3 is a partial cross-sectional side view of the antenna jacket 200. The antenna jacket 200 employs a 2D-DST (two-dimensional diffusive signal transmission) technology, which is laid open in a web site <http://www.utri.co.jp/venture/venture2.html>, in Japanese Patent Provisional Publication No. P2003-18882A. According to the 2D-DST technology, a 2D-DST substrate is configures such that a plurality of chips are distributed between two signal layers so that adjacent chips are locally and electrically connected with each other. Then, data is relayed across the plurality of chips from an origin to a destination by packets. According to the embodiment, the antenna jacket 200, which is the 2D-DST substrate in this case, is provided with two conductive sheets 212 and 214, and insulating sheets 216 and 218 for insulating the two conductive sheets 212 and 214 from outside. Between the conductive sheets 212 and 214, a plurality of communication modules 230 are distributed as schematically shown in FIG. 1.

Each of the two layers of conductive sheets 212 and 214 has flexibility and conductivity. Each of the conductive sheets 212 and 214 is formed to be a vest type jacket covering the chest and waist portion and back portion of the subject 1. The conductive sheets 212 and 214 are spaced from each other with a predetermined clearance, having the communication module 230 provided therebetween, not shown insulating layer and/or insulating sheet stacked therebetween. Thus, the conductive sheets 212 and 214 are stacked with electrically insulated from each other. The conductive sheet 212 is on the subject side, while the conductive sheet 214 is on the outer side. In other words, the conductive sheet 212 is a backside sheet of the antenna jacket 200, while the conductive sheet 214 is a front side sheet of the antenna jacket 200.

The insulating sheet 216 is a flexible sheet having an insulating property. The insulating sheet 216 is shaped and provided to cover the outer surface (i.e., a surface opposite to the surface facing the conductive sheet 214) of the conductive sheet 212. The insulating sheet 216 is made of insulating rubber, insulating film or cloth having insulating property. The insulating sheet 218 is also a flexible sheet having the insulating property, similar to the insulating sheet 216. The insulating sheet 218 is shaped and provided to cover the outer surface (i.e., a surface opposite to the surface facing the conductive sheet 212) of the conductive sheet 214. Since the insulating sheets 216 and 218 are provided, even if an electrical current flows through the conductive sheet 212 or 214, the outside of the antenna jacket 200 is insulated from the conductive sheets 212 and 214, and no electrical currents leak outside.

Next, the communication modules 230 will be described. The communication modules 230 are divided into two types of modules, which include image communication modules 230a for obtaining image signal transmitted from the capsule endoscope 100 and for transmitting radio waves to supply power and to transmit control signals, and measurement communication modules 230b for measuring body functions and obtaining measurement results (which will be referred to as body function information).

Figure 4:
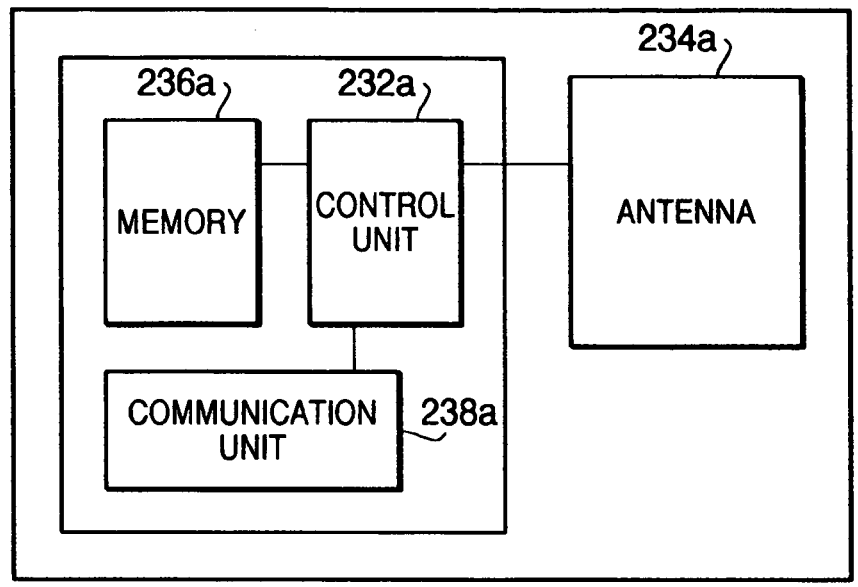
FIG. 4 is a block diagram showing a configuration of an image communication module which is one type of communication module according to the embodiment of the invention.

FIG. 4 is a block diagram showing a configuration of the image communication module 230a. The image communication module 230a includes a control unit 232a that controls the entire operation of the image communication module 230a, an antenna 234a that receives/transmits a radio wave having a predetermined frequency, a memory 236a that stores various pieces of data including ID information of the image communication module 230a, image signal and the like, and a communication unit 238a that operates to communicate with another communication module 230 located adjacent to the image communication module 230a.

The image communication module 230a has a function of receiving the image signal transmitted from the capsule endoscope 100 and a function of transmitting a radio wave for supplying power to the capsule endoscope 100 and for controlling the operation of the capsule endoscope 100, through the antenna 234a. Since power can be supplied from outside, the operator can drive the capsule endoscope 100 for a relatively long time although only a small battery can be implemented in the capsule endoscope 100.

It should be noted that the capsule endoscope 100 is mainly for capturing images inside the bowel, the image communication modules 230a being closely distributed at a corresponding area (i.e., at an area corresponding to the stomach of the subject 1).

In this embodiment, each of the image communication modules 230a is configured to receive/transmit radio wave. However, it is not necessary that each has both functions, and modules having only one of receiving and transmitting functions can be used.

As shown in FIG. 3, the conductive sheet 212 is formed with an opening 212a through which the image communication module 230a (specifically, the antenna 234a thereof) is exposed. The opening 212a enables good transmission/reception of the radio wave between the antenna 234a and the capsule endoscope 100. Since the image communication modules 230a are sandwiched between the conductive layers 212 and 214, if the opening 212a is not provided, each image communication module 230a is shielded and the radio wave cannot be transmitted to or received from the external device. Although not shown in FIG. 3, the opening 212a is formed corresponding to every one of the image communication modules 230a.

According to the embodiment, the insulating sheet 216 is provided on the outer surface of the conductive sheet 212. However, the insulating sheet 216 is not a conductive sheet, it does not serve as a shield and does not affect transmission/reception of the radio wave.

Further, according to the antenna jacket 200 configured as above, each antenna 234a is exposed to outside (with the insulating sheet 216 being interposed) through the opening 212a, and the other portion of the image communication module 230 is covered with the conductive sheets 212 and 214. Therefore, the conductive sheets 212 and 214 serves as a shield for the radio wave which is transmitted from directions other than the direction of the capsule endoscope 100 (i.e., from an external device located close to the endoscope system 10). Thus, unexpected noise directed to the antenna 234a can be shielded by the conductive sheets 212 and 214. According to another aspect, the radio wave transmitted from the antenna 234a propagates in a direction corresponding to the opening 212a, and does not affect devices located relatively close to the antenna jacket 200 or devices around the antenna jacket 200. That is, the conductive sheets 212 and 214 substantially shield or attenuate all the radio waves other than the radio wave transmitted from the capsule endoscope 100. Therefore, the antenna 234a can receive the radio wave (image signal) transmitted from the capsule endoscope 100 at a relatively high S/N ratio.

Figure 9:
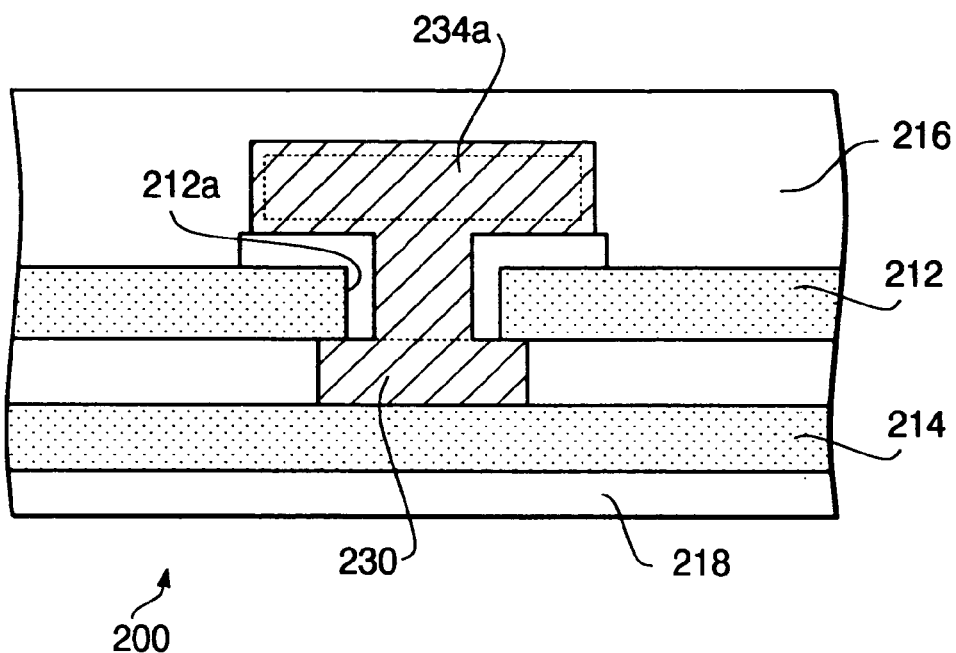
FIG. 9 shows a cross sectional structure of a jacket according to a modification of the first embodiment of the invention.

FIG. 9 shows another structure of the antenna jacket 200 according to a modification of the above-described embodiment. In this modification, at least a part of the antenna 234a is provided above the conductive sheet 212. According to this structure, in comparison with the structure shown in FIG. 3, an area of the part of the antenna 234a shielded by the conductive sheet 212 is smaller. Therefore, the receivable/transmittable angular range of the antenna 234a can be widened. That is, the function of the antenna is substantially enhanced with this structural change. This structure is particularly effective when there are no or little external devices that output radio wave around the endoscope system 10.

Further, as shown in FIG. 9, when projected on the conductive sheet 212, the area of the antenna 234a is wider than that of the communication module 230. According to this structure, it is possible to further widen the area of the antenna 234a in comparison with the structure in FIG. 3. As a result, according to the modification, it is possible to receive the image signal from the capsule endoscope 100 at a relatively high S/N ratio.

In the embodiments and modification described above, the capsule endoscope 100 and the image communication module 230a communicate with each other using a radio wave having a predetermined frequency. It is possible to modify this configuration such that the communication is performed using another spatially propagating signal. For example, light waves may be used for communication by employing a photo diode, LED (light emitting diode) or LD (laser diode). In such a case, the antenna 234a may be replaced with the photo diode. For the transmission function, the antenna 234a may be replaced with the LED or LD. Of course, if both the transmission/reception functions are implemented, both the photo diode and the LED or LD are to be employed.

Alternatively, an audio wave may be used as another form of the spatially propagating wave. When the audio wave is utilized, the antenna 234a may be replaced with a supersonic wave receiver. For transmitting the audio wave, the antenna 234a may be replaced with a supersonic transmitter. For reception/transmission, both the supersonic receiver/transmitter may replace the antenna 234a.

Figure 5:
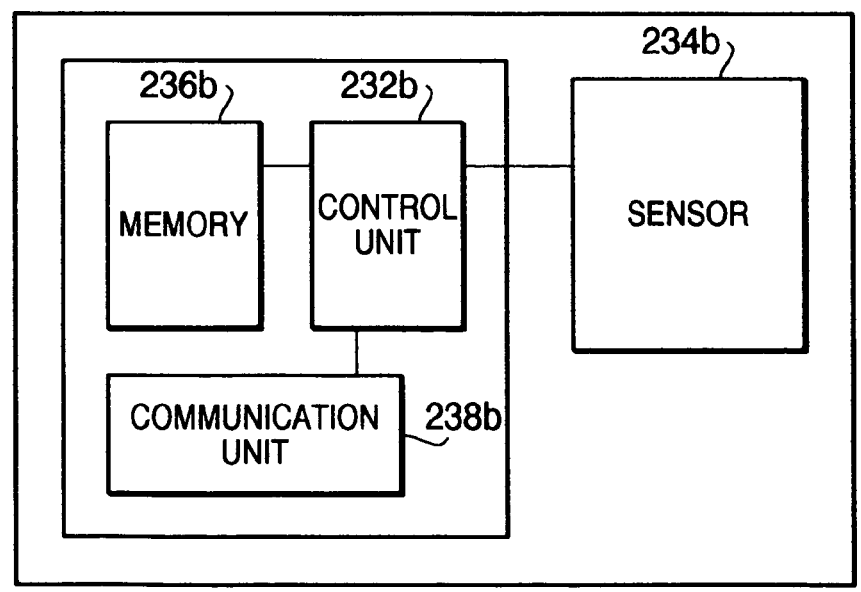
FIG. 5 is a block diagram showing a configuration of a measurement communication module which is one type of communication module according to the embodiment of the invention.

FIG. 5 shows a block diagram of the measurement communication module 230b which is one of the communication module 230. The measurement communication module 230b include a CPU 232b that controls the entire operation of the measurement communication module 230b, a sensor unit 234b for measuring body functions of the subject 1, a memory 236b for storing various pieces of data including the ID information of the module 230b and the measured body functions, and a communication unit 238b for communicating with another communication module 230 adjacent thereto.

The measurement communication module 230b mainly functions to obtain the body functions (e.g., body temperature, breathing rate, cardiac rate and the like). With use of the measurement communication module 230b, the operator can examine the body condition of the subject in addition to the image of the body cavity of the subject 1. With this function, if the subject 1 becomes ill during the observation of the body cavity, the operator can recognize the same immediately.

As described above, a lot of communication module 230 are provided between the conductive sheets, and thus a lot of measurement communication module 230b are also distributed between the conductive sheets. It should be noted that, as the sensor 234b, there are various types of sensors. For example, a temperature sensor for measuring the body temperature, a pressure sensor for measuring the breathing rate, cardiac rate or blood pressure, a Ph sensor for measuring a hydrogenion concentration, a uric acid sensor for measuring a uric acid value of sweat, a light sensor for measuring existence/unexistence of bleeding, a supersonic sensor for measuring a blood flow volume, a photo sensor for measuring an oxygen saturation degree, electrodes for cardiology measurement, and the like. The plurality of measurement modules 230b have the above sensors, respectively, and arranged at appropriate positions of the antenna jacket 200.

For example, the measurement module 230b having the pressure sensor for measuring the cardiac rate is provided at a position of the antenna jacket 200 facing a left thorax (close to the heart) of the subject 1.

The measurement module 230b mounting the temperature sensor is configured such that the sensor 234b in FIG. 5 serves as the temperature sensor such as one using a thermistor. Such a temperature sensor is mainly used for measuring the body temperature (strictly speaking, the body surface temperature) of the subject 1.

The measurement module 230b mounting the pressure sensor is configured such that the sensor 234b in FIG. 5 serves as the pressure sensor (e.g., a diaphragm type or semiconductor type pressure sensor). When the breathing rate is measured, the pressure of the body surface of the subject 1 is measured with a measuring frequency of 10 through 20 times/minute, and the number of breathing is calculated. When the cardiac rate is measured, the pressure of the body surface is measured with a measuring frequency of 50 through 100 times/minute, and the heart rate is obtained. It should be noted that the antenna jacket 200 is elasticated so that the sensors mounted thereon are press-contacted against the body surface of the subject 1. With this elasticated configuration, it is possible to press the pressure sensor against a blood vessel running close to the surface of the body to measure the blood pressure.

The measurement module 230b mounting the supersonic wave sensor is configured such that the sensor 234b in FIG. 5 serves as the supersonic wave sensor, which includes a supersonic wave receiver and transmitter (in this example, the supersonic sensor includes an integrally combined supersonic receiver/transmitter). The supersonic sensor emits a supersonic wave into the body cavity of the subject 1, and detects a Doppler shift (i.e., a change of frequency in accordance with the Doppler effect) to calculate the blood flow.

The measurement module 230b mounting the photo sensor is configured such that the sensor 234b in FIG. 5 serves as the photo sensor, which includes a light source (e.g., LED or LD) and the photo diode. In this embodiment, the sensor provided with both the light source and photo diode will be referred to as the photo sensor.

The photo sensor is used for measuring a degree of oxygen saturation in the blood, making use of the characteristic of the blood such that an absorption factor for infrared light of hemoglobin varies as the oxygen saturation degree of the hemoglobin in the blood changes. Specifically, the photo sensor functions as a reflection type photo interrupter. For example, from the LED, light is emitted to the blood inside the body cavity. Then, the reflected light is received by the photo diode to determined the status of the reflected light. Based on the detection result, the oxygen saturation degree is calculated.

The conductive sheet 212 shown in FIG. 3 is provided with openings 212b each of which increases adhesiveness of the measurement communication module 230b (sensor 234b) with respect to the subject 1 are provided. The opening 212b and the sensor 234b are formed such that the sensor 234b is fitted in the opening 212b. Since the adhesiveness is increased with use of the opening 212b, if, for example, the sensor 234b is the pressure sensor, accurate detection of the pressure is enabled.

Figure 10:
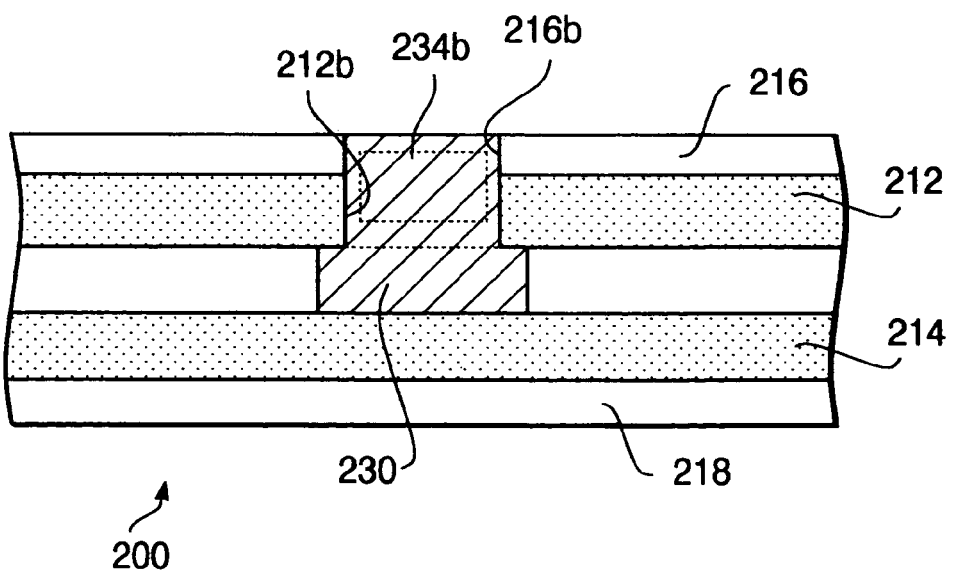
FIG. 10 shows a cross sectional structure of a jacket according to another modification of the first embodiment of the invention.

It should be noted that, as shown in FIG. 3, the insulating sheet 216 is located between the sensor 234b and the body surface of the subject 1. Therefore, strictly speaking, the sensor 234b does not directly contact the body surface. It is possible to modify the structure such that the sensor 234b directly contacts the body surface of the subject 1. FIG. 10 shows such an example, which is a modification of the structure shown in FIG. 3. As shown in FIG. 10, the insulating sheet 216 is formed with an opening 216b, which is located at a position corresponding to the opening 212b, and the sensor 234b are fitted in both the openings 212b and 216b. FIG. 10 shows only one opening 216b, but a plurality of opening 216b are formed corresponding to the opening 212b and the measuring communication modules 230b.

Among the communication modules 230, there are modules which do not have the antenna 234a or the sensor 234b. Such modules 230 includes the control unit, memory and communication unit. Such modules 230 function as relaying modules in accordance with the 2D-DST technology. That is, the communication modules 230 without the antenna 234a and the sensor 234b sequentially relay a signal (packets) when it is transmitted from a source to a destination. It should be noted that it is of course possible that the communication module 230 having the antenna 234a or the sensor 234b can also function as the relaying module.

The relaying communication module 230 (which does not have the antenna 234a or sensor 234b) can be manufactured at a low cost in comparison with that of the module provided with the antenna 234a or the sensor 234b. Further, when relaying modules are distributed, different from a case where the modules with the antenna 234a or the sensor 234b, the openings 212a or 212b need not be formed on the conductive sheet 212. Therefore, even if many relaying modules are distributed over the antenna jacket 200, the manufacturing cost will not rise so largely.

Further, providing many communication modules 230 as relaying points is advantageous in terms of the durability of the circuit (i.e., in other words, certainty in signal transmission) employing the 2D-DST technology. For example, the number of the communication modules 230 is proportional to number of selectable signal transmission paths for various signals. Since a large number of communication modules 230 are provided, even if some of them are broken, there still remain a large number of selectable signal transmission paths, and it is ensured that the image signal can be transmitted to the destination.

Next, the configuration of the control unit 220 that controls the entire operation of the antenna jacket 200 will be described. The control unit 220 mainly has a function of controlling the entire operation of the antenna jacket 200, and a function as an interface.

Figure 6:
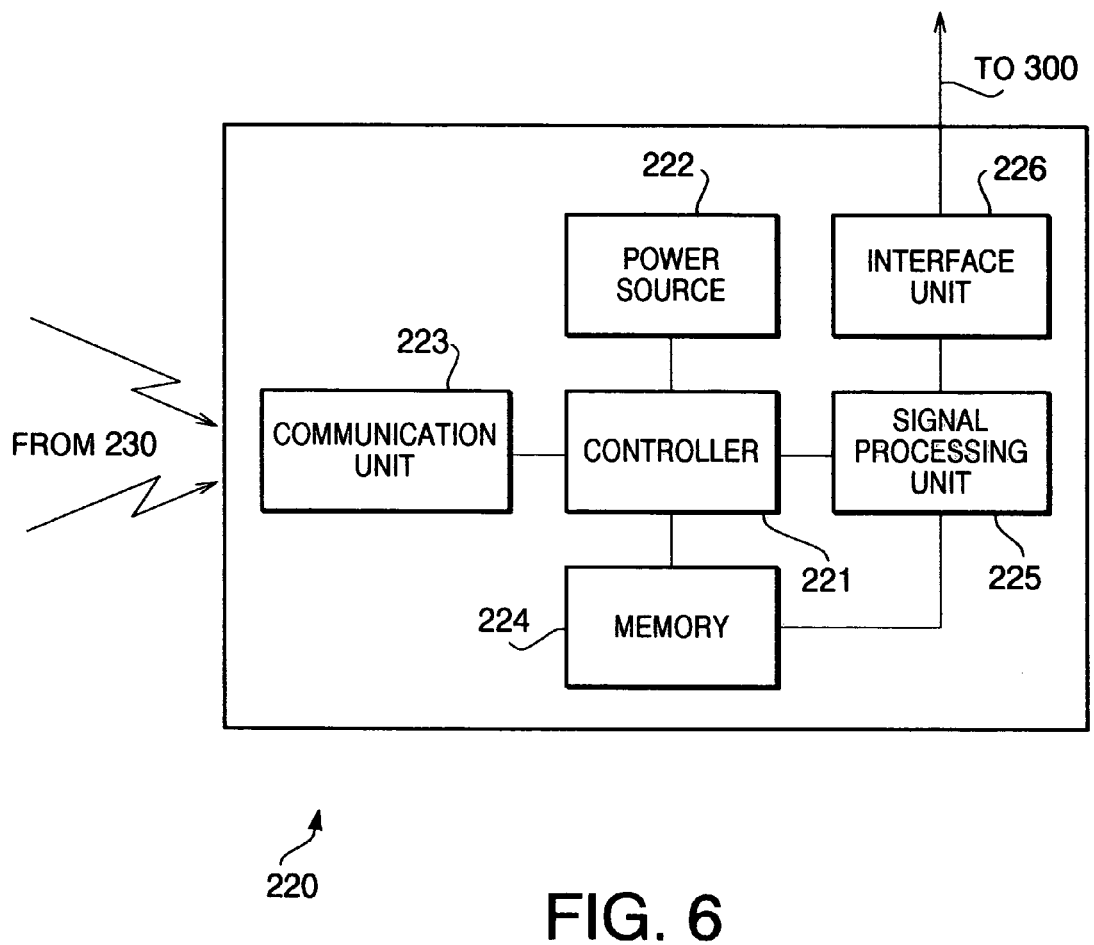
FIG. 6 is a block diagram showing a control unit employed in the endoscope system shown in FIG. 1.

FIG. 6 is a block diagram showing a configuration of the control unit 220. The control unit 220 has a controller 221 which functions as a controller for the entire operation of the antenna jacket 221, a power source 222 that supplies electrical power to the antenna jacket 200, a communication unit 223 that communicates, through the conductive sheet 212 or 214, with the communication modules 230 located close to the control unit 220, a memory 224 for storing various data including control programs and data including the obtained image signal and body information, a signal processing unit 225 that processes the obtained image signal to display an image on the display of the PC 300, and an interface unit 226 through which the control unit 220 is connected with external device and outputs data (e.g., image data and body function data) to the external device. The data obtained by respective communication modules 230 are collected by the control unit 220, which transmits the collected data to the PC 300 so that the operator can view the same on the display of the PC 300.

Figure 7:
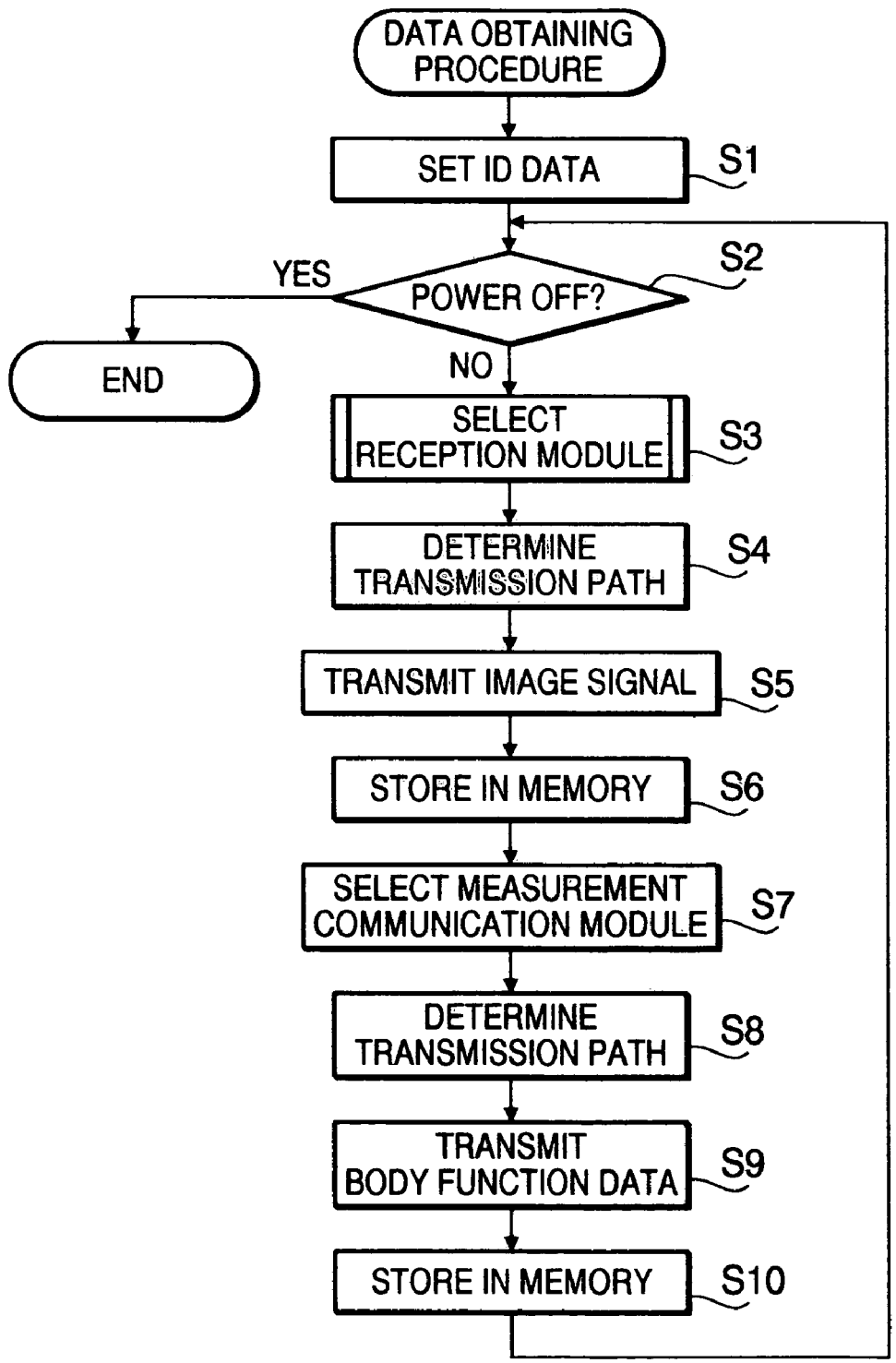
FIG. 7 is a flowchart illustrating a data obtaining procedure executed by the control unit shown in FIG. 6 according to the embodiment of the invention.

FIG. 7 is a flowchart illustrating a data obtaining procedure which is executed by the control unit 220 (i.e., the controller 221) to obtain various pieces of data including the image data and body function data.

When a power switch (not shown) of the control unit 220 is turned ON, the power source 222 supplies the electrical power to the control unit 220, thereby the control unit 220 starts its operation. Then, the controller 221 can communicate with the communication modules 230 in accordance with the 2D-DST technology. Each communication module 230 operates in accordance with an algorithm (i.e., program) stored in the control unit 232a or 232b to obtain ID information, and transmits the ID information to the control unit 220 (S1). The controller 221 can distinguish respective communication modules based on the ID information.

When the ID information setting process (S1) is finished in each communication module 230, the controller 221 judges whether the power source is switched ON or OFF (S2). If the power switch is switched OFF (S2: YES), the controller 221 finishes the procedure shown in FIG. 7. When the power switch is ON (S2: NO), controller 221 advances the procedure to S3.

In S3, the controller 221 selects an image communication module 230a that receives the radio wave output by the capsule endoscope 100. In the following description, the image communication module 230 that receives the radio wave is occasionally referred to as a reception module.

Figure 8:
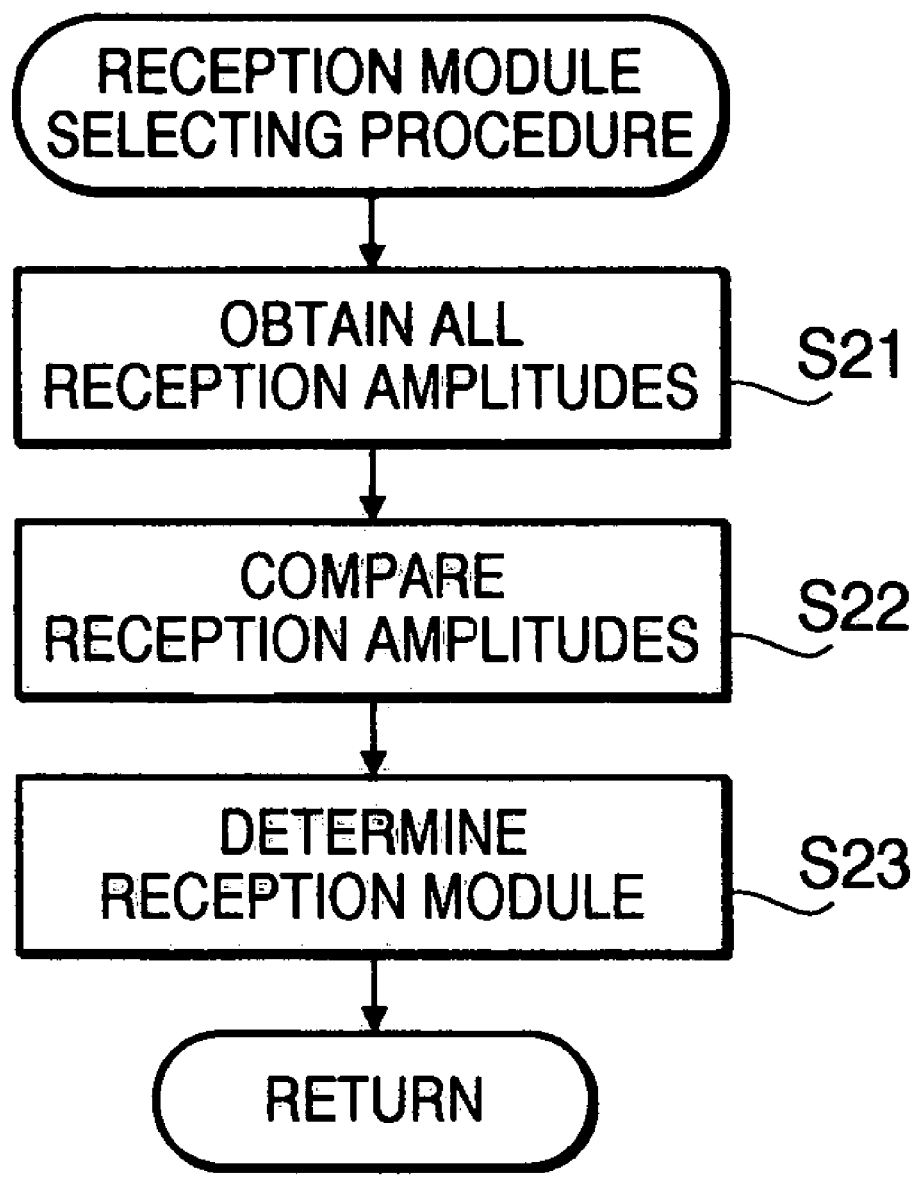
FIG. 8 is a detailed flowchart illustrating a reception module selecting procedure which is executed in the flowchart shown in FIG. 7.

FIG. 8 shows a flowchart illustrating the reception module selecting procedure which is a subroutine called in S3 of the flowchart shown in FIG. 7.

When the reception module selecting operation is called, the controller 221 obtains reception amplitude data representing a signal reception amplitude by each image communication module 230a (i.e., by the antenna 234a) regarding the image signal transmitted by the capsule endoscope 100 (S21). In S22, the signal reception amplitude data of all the image communication modules 230a distributed over the antenna jacket 200 are compared to determined the image communication module 230a having the greatest amplitude. In S23, the controller 221 selects the image communication module 230a, that has been determined to have the greatest signal reception amplitude in S21, as the module to receive the image signal transmitted from the capsule endoscope 100. Then, the controller 221 controls the selected image communication module 230a to receive the radio wave transmitted from the capsule endoscope 100. When the image communication module 234a to receive the signal is determined in S23, the reception module selecting procedure is finished, and process proceeds to S4 of FIG. 7. It should be noted that the image communication module 230a that receives the radio wave from the capsule endoscope 100 demodulates the received signal to obtain the image signal carried by the radio wave.

The image communication module 230a which is currently set to serve as the reception module transmits, under control of the controller 221, a radio wave for supplying electrical power to the capsule endoscope 100 at a predetermined timing. Since the capsule endoscope 100 is supplied with the electrical power, it can operate for a relatively long period. It should be noted that, although the reception module is used to transmit the radio wave for supplying the electrical power to the capsule endoscope in the embodiment, it is possible that another communication module 230 is used for this purpose that is not currently used for receiving the radio wave from the capsule endoscope 100. Alternatively, the communication modules 230 may include modules only for supplying the electrical power to the capsule endoscope 100.

In S4, the controller 221 determines a minimum signal transmission path which is one of paths defined by connecting the communication modules 230 from the selected reception module to the controller 221, and having the shortest path length. When the transmission path is determined, the image signal demodulated and obtained by the reception module is transmitted along the determined path and reaches the control unit 220 (S5). The controller 221 stores the thus received image signal in the memory 224 (S6). The image signal stored in the memory 224 is, under control of the controller 221, processed by the signal processing unit 225 and converted into a video signal, which is transmitted to the PC 300 via the interface 226. Thus, on the display of the PC 300, the image of the body cavity of the subject 1 is displayed.

The controller 221 selects measurement communication modules 230b to obtain body functions of the subject 1 (S7). The measurement communication modules 230b are selected in accordance with a predetermined order. For example, when step S7 is executed first time, a measurement communication module 230b having the temperature sensor is selected, and thereafter, at each execution of step S7, measurement communication modules 230b having the pressure sensor, supersonic wave sensor, photo sensor, and electrodes are selected respectively.

Alternatively, the surface of the antenna jacket 200 is divided into a plurality of areas (e.g., chest area, stomach area, etc.), and the measurement communication modules 230b in different area may be selected at every execution of step S7.

Further alternatively, if the total number of the measurement communication modules 230b provided on the antenna jacket 200 is relatively small, all the measurement communication module 230b may be selected at a time.

The control unit 232b of the selected measurement communication module 230b calculates a measurement value based on the value detected by the sensor 234b, and stores the measurement value in the memory 236b as body function data of the subject 1.

In S8, the controller 221 determines a minimum transmission path that connects the communication modules 230 from the selected measurement communication module 230b to the controller 221. When the minimum transmission path is determined, the body function data is retrieved form the memory 236b, and transmitted along the determined transmission path through the communication modules 230, and reaches the control unit 220 (S9). The body function data as received is stored in the memory 224 (S10). After storing the received body function data, the controller 221 returns to step S2, and thereafter, repeats the above-described steps S2-S10.

According to the embodiment, the body function data stored in the memory 224 is converted into a character signal by the processing unit 225, and superimposed on the video signal which is also processed by the processing unit 225. Then, the video signal is transmitted to the PC 300 via the interface unit 226. Thus, the display of the PC 300 shows characters indicating the body functions of the subject 1 as well as the image of the body cavity.

When the operator operates an operable member (not shown) for controlling the capsule endoscope 100, the image communication module 230a currently selected reception module transmits, under control of the controller 221, a control signal corresponding to the operation of the operable member to the capsule endoscope 100. With this configuration, the operator can control the operation of the capsule endoscope 100. It should be noted that the module that transmits the control signal to the capsule endoscope 100 need not be limited to the currently selected reception module 230a, but another image communication module 230a which is not currently receiving image signal can be used. Alternatively, a dedicated communication module only for transmitting the control signal may be employed.

It should be noted that the invention need not be limited to the configurations of the above-described embodiment and its modifications, but can be modified further in various ways without departing from the scope of the invention.

For example, in the embodiment, the control unit 220 and the PC 300 are connected with a cable (see FIG. 1). This can be modified such that a wireless connection may be utilized instead of the cable.

Optionally, the control unit 220 may be provided with a memory card slot so that image data and/or body function data can be stored in a memory card inserted in the card slot.

In the embodiment, the antenna jacket 200 is configured to transmit the image signal and to obtain the body function data. However, this is only an exemplary embodiment, and the jacket may be configured to have only one of the two functions.

In the embodiment, the communication modules are arranged on the jacket shaped wearable jacket. The shape of the wearable jacket need not be limited to the vest shape, but the wearable jacket may have various shapes, such as a shape of a belt.

Second Embodiment

Figure 11:
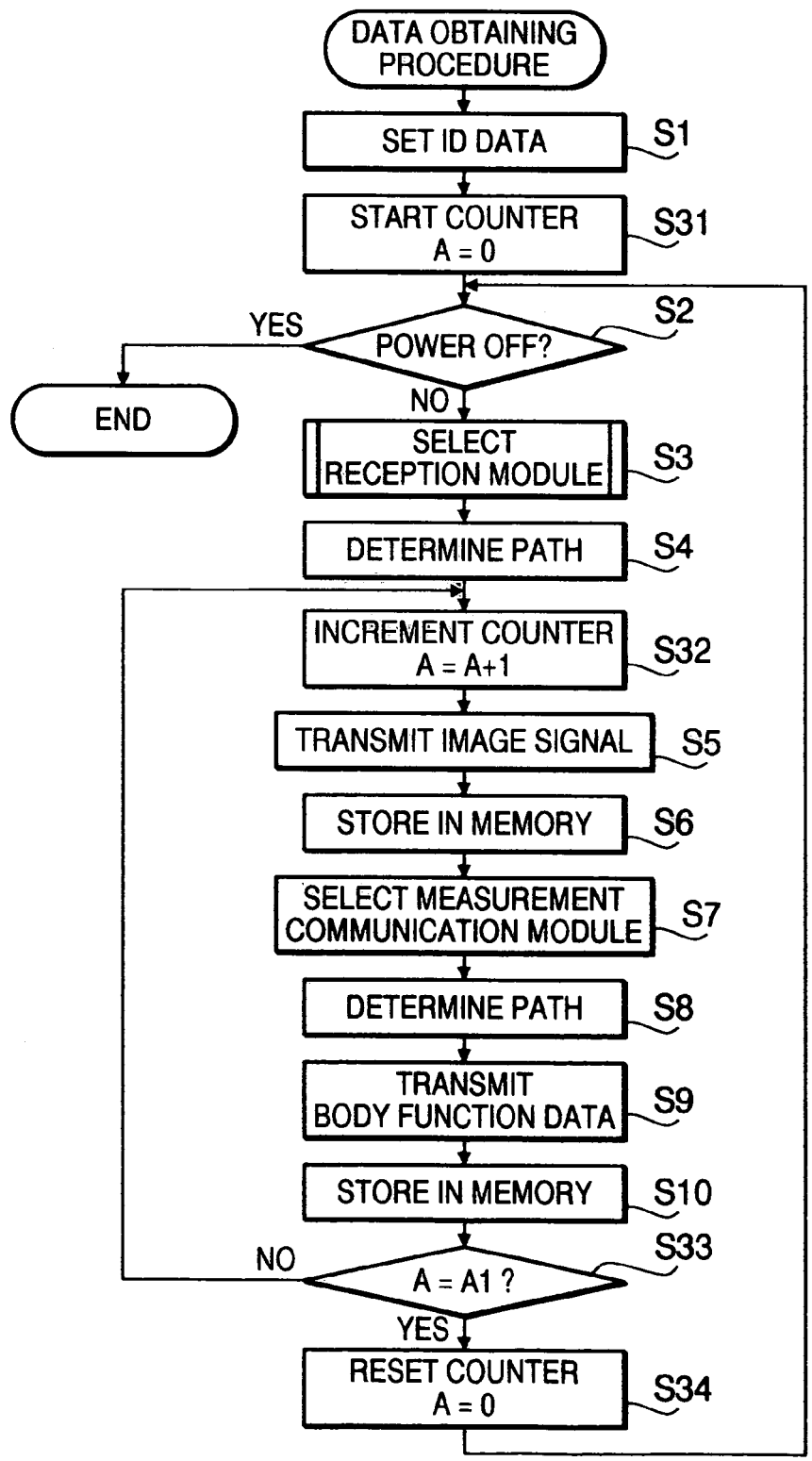
FIG. 11 is a flowchart illustrating a data obtaining procedure executed by the control unit shown in FIG. 6 according to a second embodiment of the invention.

FIG. 11 shows a flowchart illustrating a data obtaining procedure executed by the control unit 220 according to the second embodiment. According to the procedure shown in FIG. 7, the reception module is selected every time the obtained image and the body function data is stored in the memory 224. According to the second embodiment, the reception module is selected at every predetermined timing. In the following description on FIG. 11, the steps which are the same as those in FIG. 7 will be assigned with the same step numbers and description thereof will be omitted for the brevity.

When the power switch of the control unit 220 is ON and the ID data setting process is executed in S1, controller 221 starts a counter A (which has an initial value of zero) in S31. The counter A is referred to in S33, which will be described later. After controller 221 judges whether the power source is OFF in S2, and steps S3 and S4 are executed, the controller 221 increments the counter A by one.

After steps S5 through S10 are executed (i.e., the image signal and the body function data are transmitted to the control unit 220 and stored in the memory 224), the controller 221 judges whether the value of the counter A is equal to a predetermined value A1, which corresponds to a predetermined timing. If the value of the counter A is not equal to A1 (S33: NO), the controller 221 returns the process to S32, increments the counter A by one, and repeats the steps S5 through S10 again.

If the value of the counter A is equal to A1 (S33: YES), the controller 221 resets the counter A (i.e., sets the counter to zero) in S34, and the controller returns to S2.

According to the second embodiment, as described above, a period for selecting the reception module is longer than a period for transmitting the image signal and body function data to the control unit 220.

According to the procedure shown in FIG. 11, the reception module is not selected every time when the image data and body function data are stored in the memory 224, but the selection is made at every predetermined period, which is longer than the period for storing the image data and body function data in the memory 224. Therefore, according to the second embodiment, the reception module selection procedure is executed less frequently and burden to the controller 221 is decreased in comparison with the first embodiment.

The configuration of the second embodiment is particularly effective when the capsule endoscope 100 moves at a relatively low speed, since it is not necessary to change the reception module so frequently.

Third Embodiment

Figure 12:
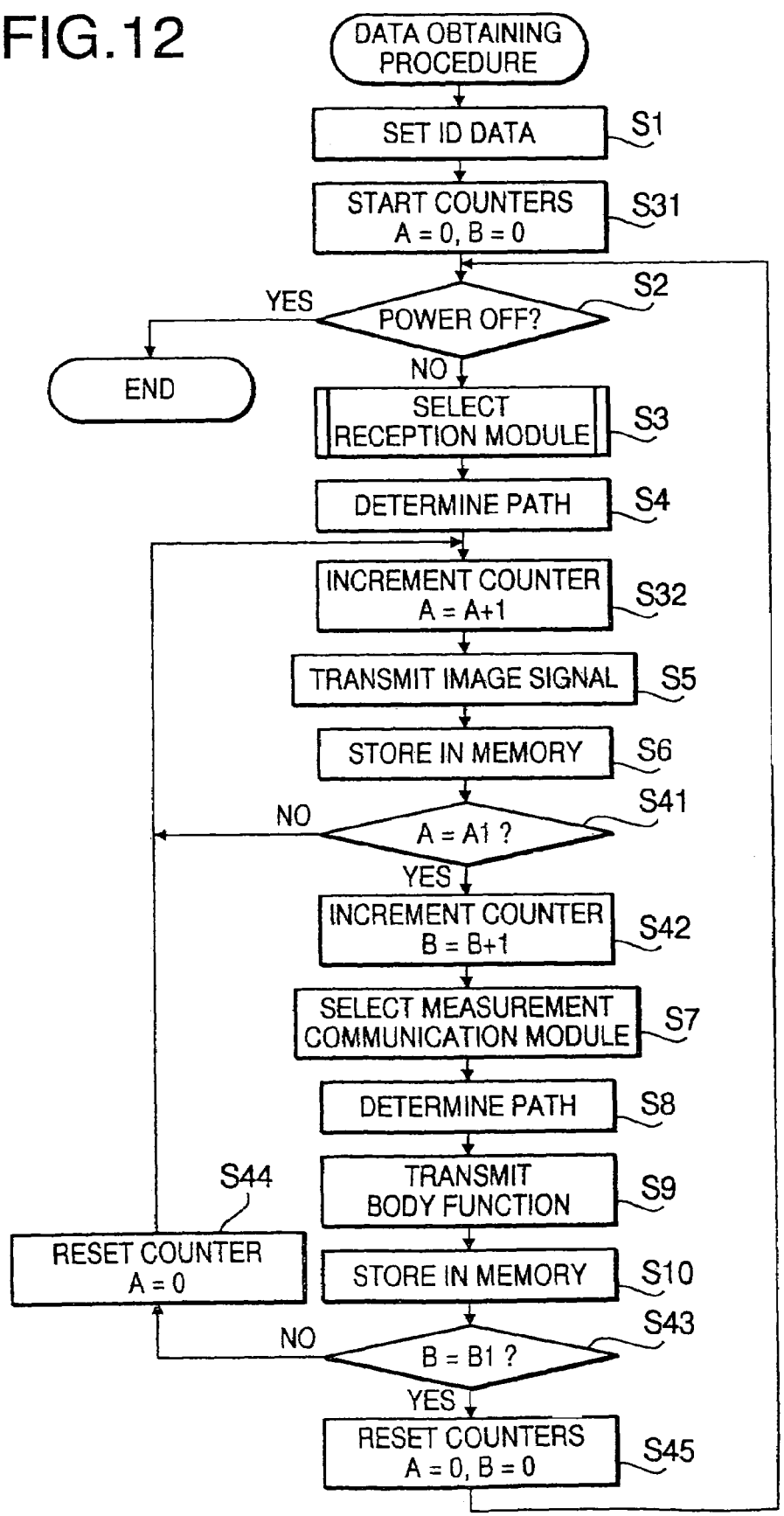
FIG. 12 is a flowchart illustrating a data obtaining procedure executed by the control unit shown in FIG. 6 according to a third embodiment of the invention.

FIG. 12 is a flowchart of the data obtaining procedure according to a third embodiment. According to the procedure shown in FIG. 12, acquisition of the image data, acquisition of the body function data and selection of the reception module are executed at different timings. It should be noted that the steps same as those in FIG. 7 or FIG. 11 will be assigned with the same step numbers and description thereof will be omitted for the brevity.

When the power switch (not shown) is turned ON and the ID data setting process is executed in S1, controller 221 starts the counters A (initial value=0) and B (initial value=0) in S31. After judgment in S2, reception module selection procedure in S3 and path determining procedure in S4 are finished, the controller 221 increments the counter A by one (S32).

When steps S5 and S6 are finished (i.e., the image signal is transmitted to the control unit 220 and stored in the memory 224), the controller 221 judges whether the value of the counter A is equal to A1 in S41. If the value of the counter A is not A1 (S41: NO), the controller 221 returns to S32, where the counter A is incremented by one (S32), and steps S5 and S6 are executed again to receive the image signal again and stores the received image signal in the memory 224.

If the value of the counter A is equal to A1 (S41: YES), the controller 221 increments the counter B by one (S42), and executes steps S7 through S10 (i.e., the body function data is transmitted to the control unit 220 and stored in the memory 224).

When step S10 is executed, the controller 221 judges whether the value of the counter B is equal to B1(S43). If the value of the counter B is equal to B1 (S43: YES), the controller 221 resets the values of the counters A and B to the initial values (=0) in S45, and the controller 221 returns the process to S2. In the above example, the interval of transmitting the body function data to the control unit 220 is longer than the interval of transmitting the image signal to the control unit 220, and further the interval of selecting the reception modules is longer than the interval of the selection of the reception module.

According to the third embodiment, the image signal and the body function data are not obtained at the same timing. The interval for obtaining the body function data is longer than the interval for obtaining the image signal. Further, according to the procedure shown in FIG. 12, the interval for selecting the reception module is longer than the timing for storing the body function data in the memory 224.

That is, according to the third embodiment, acquisition of the image data, acquisition of the body function data and selection of the reception module are executed at different timings. In particular, according to the third embodiment, emphasis is laid on the acquisition of the image data, the image data is obtained most frequently. Depending on a situation, it is possible to execute the acquisition of the body function data most frequently.

The present disclosure relates to the subject matter contained in Japanese Patent Application No. 2004-064143, filed on Mar. 8, 2004, which is expressly incorporated herein by reference in its entirety.

What is claimed is:

1. A wearable jacket having a data communication function, comprising:
    a 2D-DST substrate shaped to cover a body of a subject person,
    the 2D-DST substrate including:
        a first conductive sheet;
        a second conductive sheet; and
        a plurality of communication modules,
        the first conductive sheet and the second conductive sheet being overlapped, the plurality of communication modules being distributed between the first conductive sheet and the second conductive sheet, the plurality of communication modules being capable of communicating with adjacently arranged ones of the plurality of communication modules and relaying signals making use of at least one of conductive sheets, at least one communication module of the plurality of communication modules having a communicating system capable of communicating with an external device by at least one of receiving and transmitting a spatially propagating signal, one of the first and second conductive sheets on the external device side being formed with an area that allows the spatially propagating signal to pass through at a position corresponding to a location of a communication module having the communicating system.

2. The wearable jacket according to claim 1,
    wherein the external device is located on the first conductive sheet side, and
    wherein the area that allows the spatially propagating signal to pass through is a through opening formed on the first conductive sheet, the through opening exposing at least a part of the communication system to an outside.

3. The wearable jacket according to claim 2, wherein the communication system is arranged on the subject person side of the first conductive sheet.

4. The wearable jacket according to claim 1,
    wherein the communication system includes an antenna portion,
    wherein at least one communication module includes a circuit portion that generates a signal transmitted through the antenna portion, and
    wherein the communication system is stacked on the at least one communication module, a shape of the communication system projected on a plane of the first conductive sheet being larger than a shape of at least one communication module projected on the plane of the first conductive sheet.

5. The wearable jacket according to claim 1, wherein at least one of the plurality of communication modules is provided with a sensor that detects a body function of the subject person.

6. The wearable jacket according to claim 5, wherein the first conductive sheet is formed with a through opening which allows the sensor to contact a body surface of the subject person.

7. The wearable jacket according to claim 6, wherein the 2D-DST substrate further includes an insulating sheet that covers an outer surface of the first conductive sheet, the sensor contacting the body surface of the subject person with the insulating sheet therebetween.

8. The wearable jacket according to claim 5, wherein the sensor includes one of a body temperature sensor, a sensor for measuring a breathing rate, cardiac rate or blood pressure, a blood flow sensor, a sensor for measuring a degree of oxygen saturation, a sensor for detecting sweat, a sensor for detecting a uric acid level, a sensor for detecting an occurrence of bleeding, and electrodes for cardiographic measurement.

9. The wearable jacket according to claim 8, further comprising a data conversion system that converts values measured by the sensor into a displayable form which can be displayed on a displaying device.

10. The wearable jacket according to claim 9, further comprising a controller that controls the communication module having the communication system to transmit a received signal to the controller through the 2D-DST substrate and the communication module having the sensor to transmit measured data to the controller through the 2D-DST substrate at every predetermined period.

11. The wearable jacket according to claim 9, further comprising a controller that controls the communication module having the communication system to transmit a received signal to the controller through the 2D-DST substrate at every first predetermined period, the communication module having the sensor to transmit measured data to the controller through the 2D-DST substrate at every second predetermined period which is different from the first predetermined period.

12. The wearable jacket according to claim 11, wherein the first predetermined period is shorter than the second predetermined period.

13. The wearable jacket according to claim 11, further including a communication module selecting system that selects an optimum communication module having the communication system from among the plurality of communication modules, wherein the selection of the optimum communication module is performed at every third predetermined period which is longer than the second predetermined timing.

14. The wearable jacket according to claim 9, wherein the communication system receives a spatial propagating signal carrying an image signal, the image signal being converted into a video signal which is to be transmitted to the displaying device, the values measured by the sensor being incorporated in the video signal so that the converted values are displayed together with an image represented by the image signal in an overlapped manner.

15. An endoscope system comprising a capsule endoscope having a communication function, a wearable jacket having a communication function and a displaying device,
the capsule endoscope comprising:
an imaging device that is inserted in a body cavity and captures an image inside the body cavity; and
a wireless communicating system that transmits image data representing the captured image toward the wearable jacket,
the wearable jacket comprising:
a 2D-DST substrate shaped to cover a body of a subject person,
the 2D-DST substrate including:
a first conductive sheet;
a second conductive sheet; and
a plurality of communication modules,
the first conductive sheet and the second conductive sheet being overlapped, the plurality of communication modules being distributed between the first conductive sheet and the second conductive sheet, the plurality of communication modules being capable of communicating with adjacently arranged ones of the plurality of communication modules and relaying signals making use of at least one of conductive sheets, at least one communication module of the plurality of communication modules having a communicating system capable of communicating with the capsule endoscope by at least one of receiving and transmitting a spatially propagating signal, one of the first and second conductive sheets on the capsule endoscope side being formed with an area that allows the spatially propagating signal to pass through at a position corresponding to a location of a communication module having the communicating system.

16. The endoscope system according to claim 15, wherein the wearable jacket includes a controller that selects an optimum communication module of which a signal reception amplitude is largest from among the plurality of communication modules, the controller controlling the selected optimum communication module to execute a communication with the capsule endoscope.

17. The endoscope system according to claim 16, wherein the optimum communication module transmits a spatial propagating signal for supplying power to the capsule endoscope.

18. A wearable jacket having a data communication function, comprising:
a 2D-DST substrate shaped to cover a body of a subject person,
the 2D-DST substrate including:
at least one conductive sheet;
a plurality of communication modules,
the plurality of communication modules being distributed along a plane of the at least one conductive sheet, the plurality of communication modules being capable of communicating with adjacently arranged ones of the plurality of communication modules and relaying signals in accordance with the 2D-DST technology, at least one communication module of the plurality of communication modules having a communicating system capable of communicating with an external device by at least one of receiving and transmitting a spatially propagating signal, the at least one conductive sheet facing an external device side being formed with an area that allows the spatially propagating signal to pass through at a position corresponding to a location of a communication module having the communicating system.

19. A wearable jacket having a data communication function, comprising:
a 2D-DST substrate shaped to cover a body of a subject person,
the 2D-DST substrate including:
a first conductive sheet;
a second conductive sheet; and
a plurality of communication modules,
the first conductive sheet and the second conductive sheet being overlapped, the plurality of communication modules being distributed between the first conductive sheet and the second conductive sheet, the plurality of communication modules being capable of communicating with adjacently arranged ones of the plurality of communication modules and relaying signals making use of at least one of the first and second conductive sheets, at least one communication module of the plurality of communication modules having a sensor capable of detecting a body function of the subject.

20. The wearable jacket according to claim 19, wherein the sensor includes one of a body temperature sensor, a sensor for measuring a breathing rate, cardiac rate or blood pressure, a blood flow sensor, a sensor for measuring a degree of oxygen saturation, a sensor for detecting sweat, a sensor for detecting a uric acid level, a sensor for detecting an occurrence of bleeding, and electrodes for cardiographic measurement.

* * * * *